United States Patent
Pal et al.

(10) Patent No.: US 10,780,442 B2
(45) Date of Patent: Sep. 22, 2020

(54) CANNABIS TRICHOME SEPARATION USING CHILLED WATER

(71) Applicant: Nextleaf Solutions Ltd., Coquitlam (CA)

(72) Inventors: Krupal Pal, Burnaby (CA); Thomas Adam Ulanowski, Langley (CA); Ivan Casselman, Vancouver (CA); Ryan Delmoral Ko, Coquitlam (CA)

(73) Assignee: Nextleaf Solutions Ltd., Vancouver (CA)

( * ) Notice: Subject to any disclaimer, the term of this patent is extended or adjusted under 35 U.S.C. 154(b) by 116 days.

(21) Appl. No.: 16/278,579

(22) Filed: Feb. 18, 2019

(65) Prior Publication Data

US 2020/0261824 A1 Aug. 20, 2020

(51) Int. Cl.
| | | |
|---|---|---|
| *B02C 21/00* | (2006.01) | |
| *B01D 11/02* | (2006.01) | |
| *B01D 37/00* | (2006.01) | |
| *B02C 23/20* | (2006.01) | |
| *B01D 29/56* | (2006.01) | |
| *B02C 23/38* | (2006.01) | |
| *B02C 23/06* | (2006.01) | |
| *B02C 23/14* | (2006.01) | |
| *B02C 19/18* | (2006.01) | |
| *A24B 15/00* | (2006.01) | |
| *B02C 23/16* | (2006.01) | |

(52) U.S. Cl.
CPC .............. *B02C 21/00* (2013.01); *A24B 15/00* (2013.01); *B01D 11/028* (2013.01); *B01D 11/0257* (2013.01); *B01D 11/0292* (2013.01); *B01D 29/56* (2013.01); *B01D 37/00* (2013.01); *B02C 19/186* (2013.01); *B02C 23/06* (2013.01); *B02C 23/14* (2013.01); *B02C 23/20* (2013.01); *B02C 23/38* (2013.01); *B02C 2023/165* (2013.01)

(58) Field of Classification Search
CPC ......... B02C 21/00; B02C 23/06; B02C 23/14; B02C 23/38; B02C 19/186; B01D 11/0257; B01D 11/028; B01D 11/0292; B01D 37/00; B01D 29/56
See application file for complete search history.

(56) References Cited

U.S. PATENT DOCUMENTS

| | | |
|---|---|---|
| 6,158,591 A | 12/2000 | Delp |
| 8,640,877 B1 | 2/2014 | Pastorius |
| 9,981,203 B2 * | 5/2018 | Shuja ................. B01D 11/0226 |
| 10,646,881 B1 * | 5/2020 | Page ........................ B07B 1/36 |
| 2011/0256245 A1 | 10/2011 | Rosenblatt et al. |

(Continued)

OTHER PUBLICATIONS

Patent Cooperation Treaty International Search Report dated Mar. 27, 2020 issued for the parent application assigned International Application No. PCT/CA2020/050047 with an International Filing Date of Jan. 17, 2020.

(Continued)

*Primary Examiner* — Faye Francis
(74) *Attorney, Agent, or Firm* — Damien G. Loveland (57) ABSTRACT

*Cannabis* plant material is gently ground, mixed with chilled water and then agitated. The trichomes, being made brittle by the lowered temperature of the water, fall off the plant material during agitation. The mixture is then filtered in multiple stages to obtain the trichomes in different size fractions, which are collected separately and then dried.

18 Claims, 4 Drawing Sheets

(56) References Cited

U.S. PATENT DOCUMENTS

| | | | | |
|---|---|---|---|---|
| 2015/0181925 | A1* | 7/2015 | Turner | A24B 15/303 |
| | | | | 131/310 |
| 2017/0001200 | A1* | 1/2017 | Leffel | B02C 23/10 |
| 2017/0188623 | A1* | 7/2017 | Cranford | A61K 31/352 |
| 2018/0339298 | A1* | 11/2018 | Mayers | G01G 17/02 |
| 2018/0344790 | A1* | 12/2018 | Vu | A24B 15/16 |
| 2018/0352848 | A1* | 12/2018 | Vu | A24D 1/18 |
| 2019/0104887 | A1* | 4/2019 | Tussey | A47J 42/34 |
| 2019/0118187 | A1* | 4/2019 | Nahtigal | B02C 18/2216 |
| 2019/0134125 | A1* | 5/2019 | Vu | A24B 15/303 |
| 2019/0168232 | A1* | 6/2019 | Bruggemann | B02C 17/1855 |
| 2020/0086229 | A1* | 3/2020 | Ko | B01D 11/028 |
| 2020/0108018 | A1* | 4/2020 | Shadurin | A24D 1/02 |
| 2020/0222910 | A1* | 7/2020 | Nahtigal | B02C 18/2216 |

OTHER PUBLICATIONS

Patent Cooperation Treaty Written Opinion of the International Searching Authority dated Mar. 27, 2020 issued for the parent application assigned International Application No. PCT/CA2020/050047 with an Internation Filing Date of Jan. 17, 2020.

Extraction Magazine, "Washing Lost Art of the Hashishin Workshop". YouTube, Oct. 17, 2018, (online) [retrieved on Apr. 8, 2020]. Retrieved from the Internet: https://www.youtube.com/watch?v=4Z8PJvOPx8M.

* cited by examiner

CANNABIS TRICHOME SEPARATION USING CHILLED WATER

TECHNICAL FIELD

This invention relates to a method for refining raw *cannabis* plant material. More specifically, it relates to a method for separating cannabinoid rich trichomes from raw *cannabis* plant material using chilled water and filtration techniques.

BACKGROUND

In legal, adult-use markets, sales of extracts are growing ten times faster compared to the sales of dried *cannabis*, and extracts account for over 60% of revenue. With legalization, consumer preferences are shifting from dried *cannabis* to extracted *cannabis* products, and it is therefore desirable to provide products with fewer impurities to the consumers, different flavors and perhaps new ways of consumption. Thus, the development of new and improved refinement and extraction techniques is important for the *cannabis* industry.

Most psychoactive substances are contained in parts of the *cannabis* plant that are called trichomes, which can be defined as an epidermal glandular outgrowth part of the plant. It is usually necessary to separate these trichomes from the raw *cannabis* plant material to produce *cannabis* products.

This background is not intended, nor should be construed, to constitute prior art against the present invention.

SUMMARY OF INVENTION

Intermediary *cannabis* products are created in such a way that a high content of active ingredients is targeted. Thus, physically isolating the trichomes from the raw *cannabis* plant material before running a chemical extraction process helps to improve upfront the quality of the final *cannabis* products, and such isolation can be assimilated as an initial refinement step.

Beside this first aspect, there are various forms of trichome in the *cannabis* plant. Each type has a certain size or active substance content, for example, and therefore will exhibit various degrees of purity. Thereby, the separation of these different forms of trichome is important for choosing the most appropriate starting material for a further extraction process and to obtain final cannabinoid products with a high cannabidiol (CBD), cannabigerol (CBG), tetrahydrocannabinol (THC), and/or other cannabinoid content.

The present invention separates trichomes from raw plant material using chilled water and a filtration setup. The raw *cannabis* plant material is first gently ground, allowing it to be broken up and causing larger, three-dimensional flowers to present a larger exposed surface area. The gently ground plant matter is then mixed or agitated in chilled water to separate the trichomes from the raw *cannabis* plant material. Next, the mixture is filtered through multiple stages to retain at least one fraction of *cannabis* plant matter that is rich in trichomes. In a last step, the desired residue is dried to obtain a fine powder rich in trichomes.

Disclosed herein is a process for separating trichomes from raw *cannabis* plant material comprising: grinding the raw *cannabis* plant material using a mesh size between 1 cm and 2.5 cm to result in ground raw *cannabis* plant material; adding water at a temperature below 10° C. to the ground raw *cannabis* plant material to form a mixture; agitating the mixture to separate trichomes from the ground raw *cannabis* plant material; straining the mixture using a coarse mesh with a pore size of 200-1000 μm to separate the mixture into a trichome filtrate and unwanted *cannabis* plant matter; filtering the trichome filtrate to retain a residue of trichome-rich *cannabis* plant matter; and drying the trichome-rich *cannabis* plant matter to form a powder.

In some embodiments, the temperature of the water is 0-5° C., the process comprising maintaining the water at a temperature between 0-5° C. In some embodiments, the mixture is agitated with a blunt agitator that rotates at a speed of 50-500 rpm.

BRIEF DESCRIPTION OF DRAWINGS

The following drawings illustrate embodiments of the invention, which should not be construed as restricting the scope of the invention in any way.

DESCRIPTION

A. Glossary

Cannabidiol (CBD) refers to a phytocannabinoid molecule that is present in *cannabis* plants.

Cannabidiolic acid (CBDa), is a cannabinoid produced on the stems, leaves and flowers of some varieties of *cannabis* plants.

Cannabigerol (CBG) is a non-psychoactive cannabidiol usually present in smaller amounts in *cannabis*.

Cannabinoids are a group of chemicals that act on cannabinoid receptors in the body, numerous of which are found in the *cannabis* plant.

A filter refers to a device that is generally used to separate elements or particles from mixtures or to characterize a range of particle sizes. A filter system is a series of filters of different pore sizes arranged in decreasing order.

A filtrate refers to a substance that passes through a filter.

A residue is the material that is retained by a filter.

Tetrahydrocannabinol (THC) refers to a phytocannabinoid molecule that is present in the *cannabis* plant and known for its psychoactive effect when consumed or inhaled.

Tetrahydrocannabinolic acid (THCa) is produced by the *cannabis* plant and is the non-intoxicating form of THC. THCa is mostly present in raw *cannabis*; THCa forms THC when heat is applied, typically by combustion.

Trichomes refer to fine outgrowths or appendages that can be found on the *cannabis* plant.

B. Overview

Figure 1:
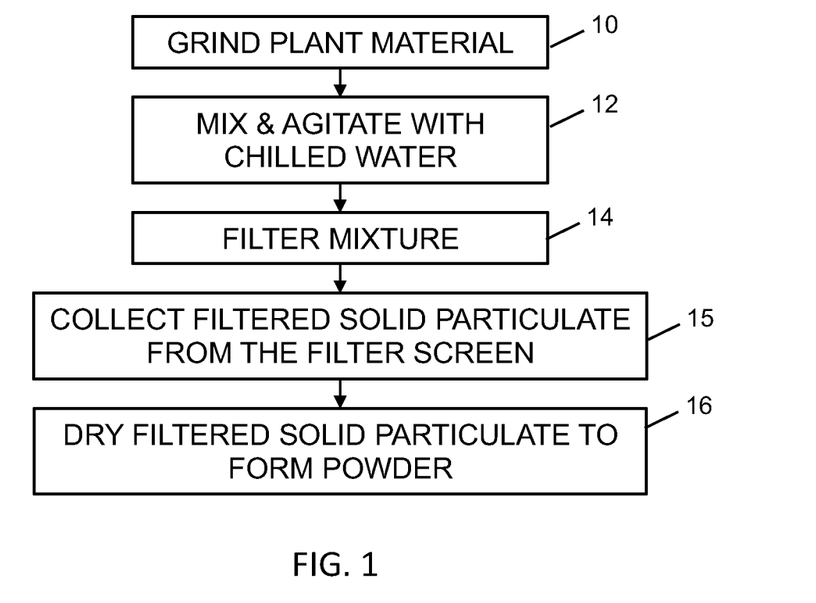
FIG. 1 is a high-level flowchart describing the key steps for separating the trichomes from the raw *cannabis* plant material according to an embodiment of the present invention.

Referring to FIG. 1 there is shown the key steps of the process for separating trichomes from raw *cannabis* plant material. In step 10, the raw *cannabis* plant material, or biomass, is gently ground by means of a grinder of the type generally used in the manufacture of pharmaceuticals. In step 12, the ground raw *cannabis* plant material is mixed and agitated with chilled water for an extended period of time to separate the trichomes from the rest of the plant material. Tap water is acceptable for use, provided that it is potable. Filtered water would also be acceptable. Next, the ground raw *cannabis* plant material and water mixture is filtered in step 14 in order to collect the trichomes from the mixture. The filtering 14 generally includes multiple filtration steps with decreasing mesh sizes, including an initial coarse mesh to remove unwanted biomass. At least one fraction of the *cannabis* plant matter retained by the filter in cake form is rich in trichomes. Finally, the *cannabis* plant matter rich in trichomes is dried in step 16 to decrease the level of moisture of the trichomes, resulting in a fine *cannabis* powder rich in trichomes.

Figure 2:
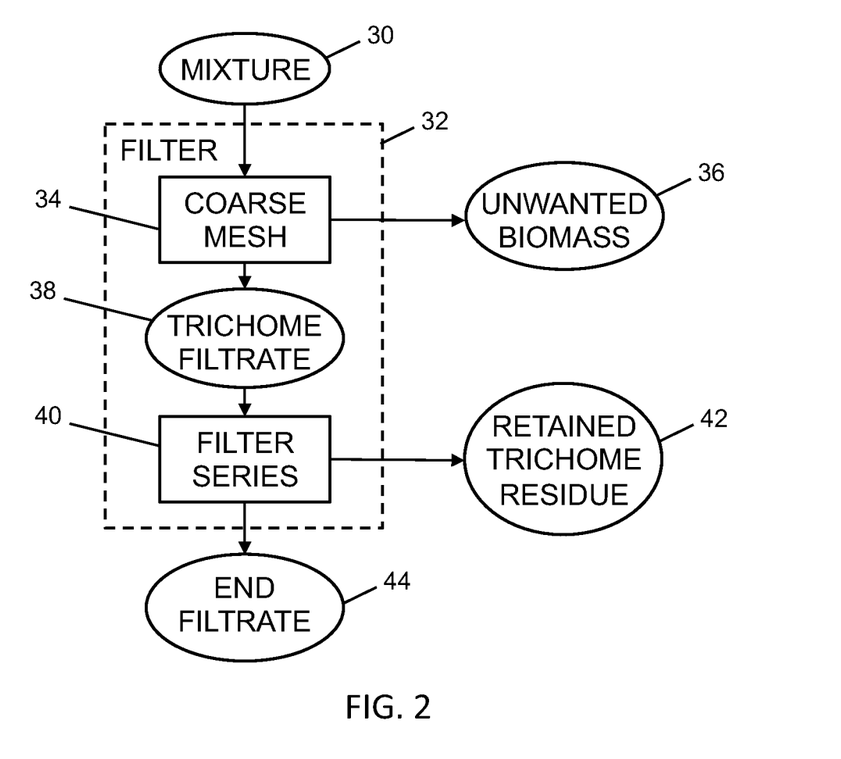
FIG. 2 is a schematic overview of the substances involved in the process in relation to the filter system, according to an embodiment of the present invention.

Referring to FIG. 2, the mixture 30 of ground raw *cannabis* plant material and chilled water, after having been mixed for an extended period of time, is passed to the filter system 32. The first component of the filter system 32 is a coarse mesh 34, which separates the mixture into unwanted biomass 36 and a trichome filtrate 38, which carries the trichomes that have been separated from the bulk of the ground raw *cannabis* plant matter (i.e. the unwanted biomass). The trichome filtrate 38 is passed through a filter series 40 to result in a retained trichome residue 42 and a brownish, chlorophyll-rich end filtrate 44, which has little or no value.

C. Exemplary Process

Figure 3:
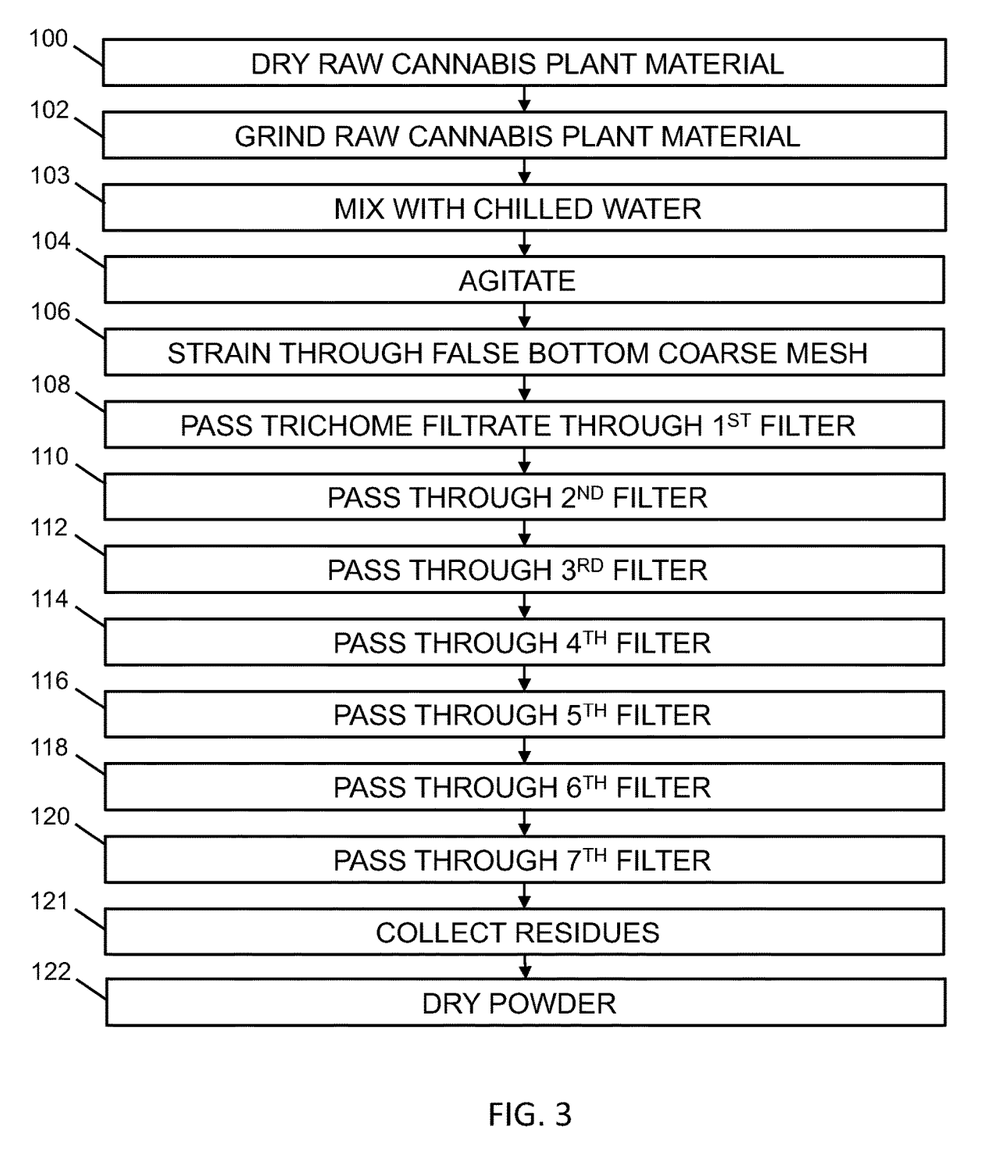
FIG. 3 is a detailed flowchart describing the steps for separating the trichomes from the raw *cannabis* plant material according to an embodiment of the present invention.

Referring to FIG. 3 there is shown in more detail the steps of the process used to separate the trichomes from the raw *cannabis* plant material. Any strain of *cannabis* can be used in the process, and any part of the *cannabis* plant above ground level can be used, i.e. including stem, leaves, buds and flowers. In a first, optional step 100, the raw *cannabis* plant material is dried. Ideally, the moisture content of the raw plant material after drying is 10% or below, by weight. Then in step 102, the raw *cannabis* plant material is ground. The grinding step 102 is achieved using a grinder with a mesh size that is between 1 cm (⅜ in) and 2.5 cm (1 in). Such grinders are used in the pharmaceutical industry for gentle size reduction processes. The grinding is partial (i.e. to a piece size defined by the mesh, rather than to a smaller size) and is conducted in such a manner that parts of the raw *cannabis* plant material are reduced to an optimized size for the subsequent mixing and agitation steps. This partial grinding process reduces the size of the *cannabis* pieces, which helps to expose more of the *cannabis* plant's surface area (e.g. buds) so that the agitation step is more efficient. On the other hand, the size of the ground raw *cannabis* plant material is kept large enough so that unwanted *cannabis* plant material does not pass through the coarse mesh 34 and contaminate the residue, or clog parts of the system such as the agitator. By not grinding the plant so small, fewer cuts are made in the plant material, which limits the quantity of small pieces of unwanted plant material that are broken up. It is likely that some of the trichomes are separated from the biomass or broken up during the grinding process, which is acceptable as the trichomes or trichome parts will be retained by the filtering.

In step 103, the ground raw *cannabis* plant material is mixed (or flooded) with chilled water in a mixing vessel equipped with a cooling jacket. In step 104, the ground raw *cannabis* plant material and chilled water are agitated in the mixing vessel. Agitation of the mixture causes the breakage of the trichomes from the *cannabis* plant material, the separation of the trichomes away from the *cannabis* plant material and the suspension of the separated trichomes and trichome parts in the water. The agitation during step 104 is provided by the implementation of a blunt agitator in the mixing vessel, for example, or the use of compressed air to create bubbles in the mixture, which is a gentler process. If an agitator is used, it should not be sharp enough to cut the biomass, as its purpose is simply to physically move and stir the mixture.

The temperature of chilled water used for mixing is maintained at or below 5° C. during mixing. The temperature in the mixing vessel is maintained using chilled water as a chilling agent in the mixing vessel's cooling jacket. The freezing point of water is 0° C., and a temperature above 4-5° C. starts to reduce the brittleness of the trichomes. Maintaining the temperature in the mixing vessel from 0 to 5° C. facilitates the breaking apart of the trichomes, since in this temperature range they are more brittle compared to higher temperatures. Nevertheless, the process in some embodiments is carried out with a water temperature between 0-10° C., because there is still some, albeit reduced, brittleness of the trichomes between 5-10° C., but above 10° C. there is too little brittleness for the agitation step to be effective.

The ground raw *cannabis* plant material and chilled water mixture is agitated slowly in order to prevent further contamination of the final product with unwanted parts of the *cannabis* plant. Indeed, the more aggressive the mixing, the more breakage of raw *cannabis* plant material may occur. Therefore, the probability of breaking parts of the plant that do not contain trichomes, such as pistils and small bits of leaves, is increased. These parts of the plant that do not contain trichomes may decrease the purity of the fine *cannabis* powder or the final products made using the powder, however, the overall yield may be increased as the more aggressive or prolonged agitation would also have removed more trichomes. The purpose of the agitating is also to disperse the separated trichomes into the water. The correct speed for the agitating step should be defined with regards to the mixing vessel size and the amount of ground raw *cannabis* plant material to be processed. The duration of the agitating step is based on the input material quality, speed of agitation, and objectives such as yield or purity of the *cannabis* powder product.

As an example, the agitation process uses a mixing vessel. The capacity of the mixing vessel is 50 L, the cooling jacket capacity is 16 L, and the agitator is a pitched blade turbine. In a mixing vessel this size, 1-2.5 kg of biomass is appropriate. The speed of rotation of the agitator is between 50 and 500 rpm (revolutions per minute), depending on the volume of mixture in the mixing vessel. Usually, the speed is set to at least 150-200 rpm. The diameter of the agitator is typically ⅓ the diameter of the mixing vessel. The duration of the agitation is in the range of 5 to 120 min, for example.

In some embodiments, a packed bubble column or fluidized bed is used to agitate the ground raw *cannabis* plant material in the water. Compressed air is fed into the mixture of water and ground raw *cannabis* plant material, which can result in a gentler agitation process than using an agitator. A rotatory drum into which the mixture is placed is used in other embodiments to agitate the mixture.

The ground raw *cannabis* plant material and chilled water mixture is strained through to a coarse mesh (e.g. coarse screen false bottom) with a pore size of 200-1000 µm in step 106. During this step, the largest, non-trichome parts of the raw *cannabis* plant material (leaves, stems, etc.) are retained to prevent them reaching the series of residue capturing filters. Thus, the passing filtrate carries a substance that can be described as *cannabis* plant matter that has a higher content in trichomes than the raw *cannabis* plant material. The passing filtrate is referred to as a trichome filtrate. The pre-filter coarse screen retains unwanted plant matter in sizes from 200-1000 µm upwards, depending on the mesh size of the screen.

Then, in steps 108-120, the trichome filtrate is filtered through a succession of filters with decreasing mesh sizes arranged in series. The purpose of this series of filtration steps is to obtain desired particle size ranges (i.e. fractions) of *cannabis* plant matter rich in trichomes. Each filter in the series of filters retains the desired particle size, leaving the trichome filtrate, now with depleted trichomes, to pass through to the next filter in the series. In some embodiments, the filters are replaced by sieves. In step 108, the trichome filtrate is added to a first filter with a pore size of 180-212 µm. In step 110, the filtrate that has passed through the first filter is passed through a second filter with a pore size of 150-180 µm. In step 112, the filtrate that has passed through the second filter is passed through a third filter with a pore size of 106-150 µm. In step 114, the filtrate that has passed through the third filter is passed through a fourth filter with a pore size of 75-90 µm. In step 116, the filtrate that has passed through the fourth filter is passed through a fifth filter with a pore size of 63-75 µm. In step 118, the filtrate that has passed through the fifth filter is passed through a sixth filter with a pore size of 32-53 µm. In step 120, the filtrate that has passed through the sixth filter is passed through a seventh filter with a pore size of 15-32 µm. In other embodiments, the number of filters varies between 3 and 15. Mesh numbers may instead be used to specify the filter pore sizes.

The *cannabis* plant matter rich in trichomes is retained by and/or collected on each filter or sieve in the filter series. As a result, every fraction of *cannabis* plant matter collected has particles within a size range that is determined by the mesh sizes of the upstream and downstream filters.

Since the filtering is a size-based separation process, any part of the plant that is small enough can hypothetically pass through one or more of the filtering screens. The amount of non-trichome material present after the extraction is largely based on the strength of agitation. When the applied agitation is strong, the purity level of the product is compromised, while when the applied agitation is weak the product has a good purity but is obtained in lower yields. In addition, variations in the percentage content by weight in trichomes may be observed depending on the agitation duration and the quality of the input material.

Each fraction of the retained *cannabis* plant matter is then collected separately in step 121. The collected fractions are then dried using any of various drying techniques in step 122 in order to result in *cannabis* plant matter rich in trichomes in the form of a fine, dry powder. On an industrial scale, a conveyor dryer with a temperature set between 30 and 40° C. can be used to dry the filtered *cannabis* plant matter. In some embodiments, the moisture may be measured after the drying step. Any significant amount of water left in the powder after the filtration may promote the growth of mold. The mold may alter or degrade the quality of the product. Ideally, therefore, the water percentage content by weight is below 10%.

Typically, the goal is to separate as much trichome material as possible from the raw *cannabis* plant material, without breaking up and concentrating leaf/plant tissue during the process. The yield depends on the quality of input materials; some *cannabis* has a lot of trichomes, and some has very little. One typically aims for about 5-15% of the weight of the input material, but this is a very rough estimate. Each fraction of obtained *cannabis* powder typically has a different strength. Usually, the optimum size to concentrate trichome heads is 60-100 µm.

In some embodiments, a decarboxylation step is added to decarboxylate the fine dry *cannabis* powder. This decarboxylation process is used to convert the tetrahydrocannabinolic acid (THCa), contained in the fine dry *cannabis* powder, into the psychoactive compound THC. The fine dry *cannabis* powder is decarboxylated by heating the powder with a temperature set between 115-120° C. for 90 min. or more.

D. Exemplary Apparatus

Figure 4:
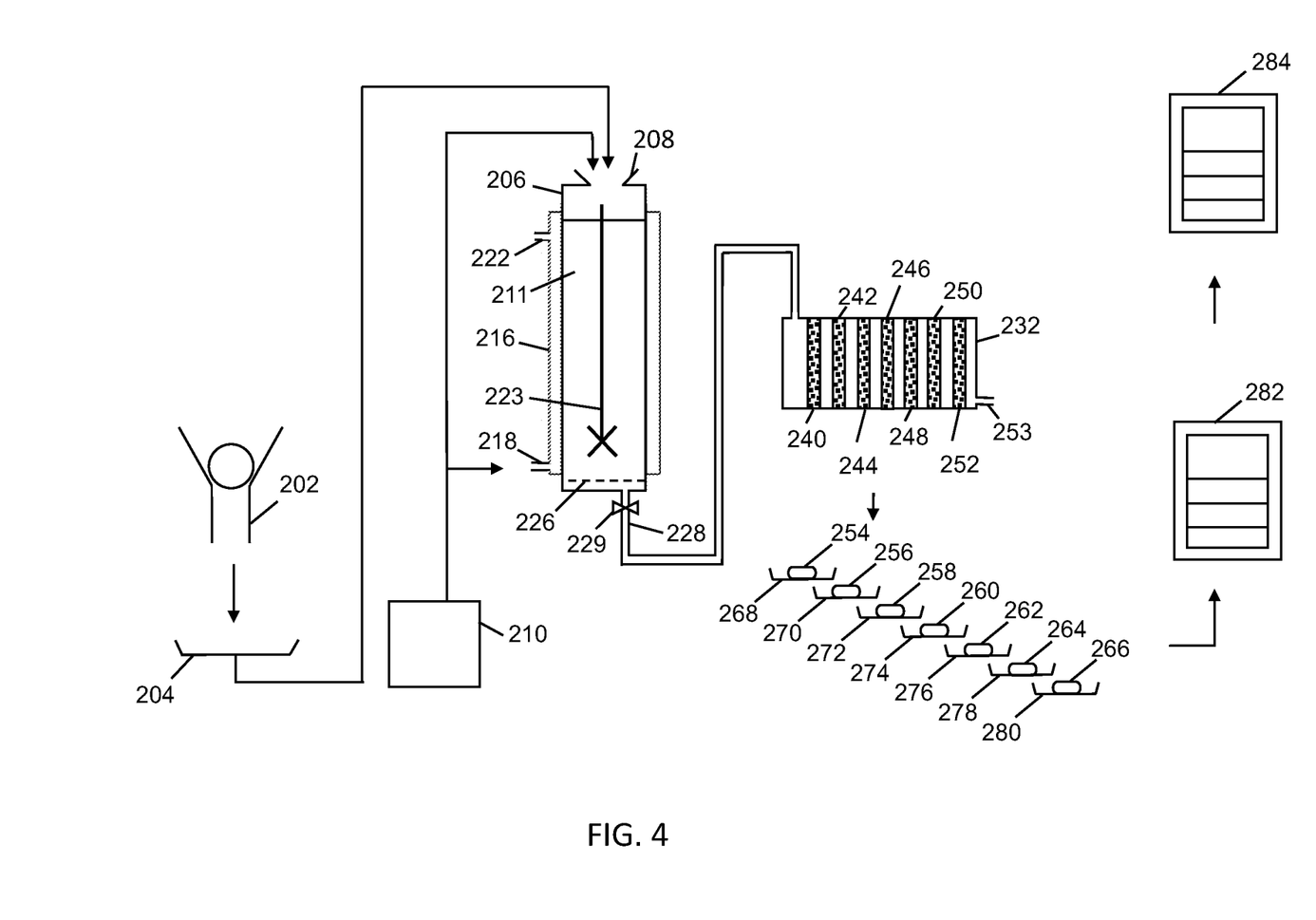
FIG. 4 is a schematic diagram of the apparatus used to separate the trichomes from the raw *cannabis* plant material according to an embodiment of the present invention.

Dried raw *cannabis* plant material is first placed in a grinder 202. The grinder 202 gently breaks the raw *cannabis* plant material down. In addition, the grinder 202, by coarsely breaking the raw *cannabis* plant material into smaller parts, facilitates a better efficiency for separating the trichomes from the raw *cannabis* plant material in the subsequent steps. The ground raw *cannabis* plant material is then collected on a tray 204.

After that, the raw *cannabis* plant material is introduced into a mixing vessel 206 through an opening 208 at the top part of the vessel. The mixing vessel is made of stainless steel, glass or plastic such as HDPE (high density polyethylene)

Chilled water contained in a vessel 210 is poured or otherwise fed into the mixing vessel 206 via the opening 208 at the top part of the mixing vessel to form mixture 211. A cooling jacket 216 is mounted around the mixing vessel 206. This type of cooling jacket 216 can usually host a liquid whose temperature is from 0° C. to −80° C. The cooling jacket 216 has one inlet 218 at its bottom part where the chilled water from the vessel 210 is introduced, e.g. by way of a pump or a pressurized line. The chilled water is introduced into the cooling jacket 216 until it reaches an overflow outlet 222 located at the top part of the cooling jacket. In some embodiments, the cooling water is circulated through the cooling jacket 216 and its temperature is continually monitored.

The mixture 211 of water and ground raw *cannabis* plant material is maintained at 0-5° C., for example, by the cooling jacket 216 during the agitation. The agitator 223 is a blunt device that rotates about the axis of the vessel 206 at a speed of 50-500 rpm. Any structure of agitator, from simple to complex, including those with paddles or pitched blades, is acceptable for the agitation process, provided that it has no cutting edges.

At the bottom of the vessel 206, there is a coarse mesh false bottom 226. After the ground raw *cannabis* plant material has been mixed with the water, the mixture is drained through the coarse mesh 226, which retains unwanted biomass, and the trichome filtrate exits vessel 206 via pipe 228 and valve 229.

The trichome filtrate is then transferred to a series of seven filter presses 232 via the pipe 228. The valve 229 controls the release of the trichome filtrate into the series of filter presses 232.

The filter presses each may be of a filter press, plate and frame filter design, sometimes known as a membrane filter plate. Each filter press typically includes multiple plates and frames. Each series of filters is pressurized by a pump to help the liquid pass through all the filters, and to make sure that suspended solids do not settle in the system. The cannabis plant matter rich in trichomes that is retained by each filter can be described, in terms of its physical characteristics, as a compressed cake. The cakes are removed, for example, by shaking the filters or by gently scraping them. In this embodiment, a plate/frame filter press is needed for each size of filter, since all filters in a given plate/frame press have the same pore size. An advantage of using a filter press is that it is easy to remove and replace individual screens.

The slurry of water and trichomes may be pumped into the filter press series 232, where it is dewatered under pressure. The applied pressure depends on the geometry and size of the filter presses, as well as the cake's thickness. The end filtrate, from which substantially all trichomes have been filtered out, is not required for further filtering and is discharged through outlet 253. The end filtrate, however, could be recirculated if it is suspected that the filters have not been functioning properly.

Within the filter press series 232, the trichome filtrate is successively passed through a first filter press 240 with a pore size of 180-212 µm, a second filter press 242 with a pore size of 150-180 µm, a third filter press 244 with a pore size of 106-150 µm, a fourth filter press 246 with a pore size of 75-90 µm, a fifth filter press 248 with a pore size of 63-75 µm, a sixth filter press 250 with a pore size of 32-53 µm and finally a seventh filter press 252 with a pore size of 15-32 µm. In another embodiment, the filter presses are defined by and use industry-standard mesh sizes, such as a series of multiple filter presses starting with a filter press with a mesh number of 60 (250 µm) and ending with a final filter press with a mesh number of 230 (63 µm) or higher. After that, the retained plant matter 254, 256, 258, 260, 262, 264 and 266 from each filter press 240, 242, 244, 246, 248, 250, 252 is collected on separate trays 268, 270, 272, 274, 276, 278 and 280. The trays 268, 270, 272, 274, 276, 278 and 280 are then further placed in an oven 282 set at 30-40° C. to proceed to drying.

Optionally, the trays 268, 270, 272, 274, 276, 278 and 280 with the dried trichomes are then positioned in another oven 284 set at 115-120° C. to proceed to decarboxylation, or in other embodiments the dried trichomes are decarboxylated in the same oven 282 at a higher temperature than that used for drying.

Figure 5:
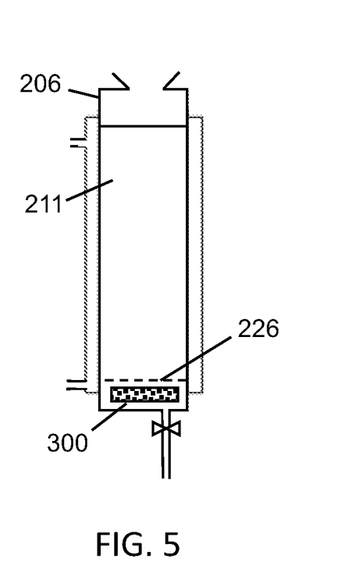
FIG. 5 schematically shows an embodiment of the mixing vessel in which a fluidized bed is used to agitate the mixture, according to an embodiment of the present invention.

FIG. 5 shows an example of the apparatus in which a fluidized bed 300 is located at the bottom of the mixing vessel 206. In this embodiment, a rotating agitator 223 is not needed. The fluidized bed, or sparger or other diffusion device introduces bubbles of gas into the mixture 211, which pass up through the coarse mesh false bottom 226 and agitate the mixture as they rise.

E. Further Variations

In some embodiments, fresh raw cannabis plant material is ground directly without being previously dried. Preferably, however, the raw cannabis plant material is dry.

In other embodiments, the starting material is frozen cannabis plant material. The cannabis plant material is frozen from fresh or after drying it.

Figure 6:
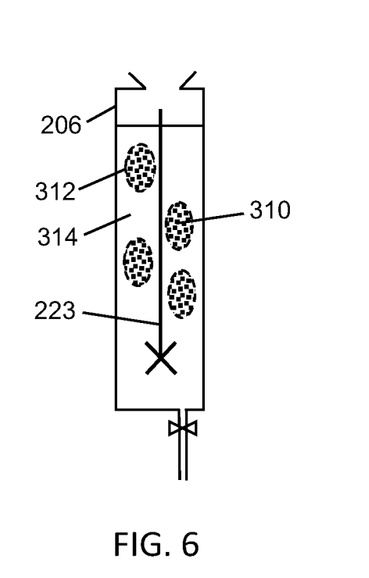
FIG. 6 schematically shows an embodiment of the mixing vessel in which the ground raw *cannabis* plant material is placed into mesh bags in the mixing vessel, according to an embodiment of the present invention.

In some embodiments, the ground cannabis plant material is put into one or more 200-1000 micron nylon mesh bags before being added to the chilled water. The bags help retain the unwanted biomass, but allow the separated trichomes to pass through during the agitation step. FIG. 6 shows an embodiment of the mixing vessel 206 in which the ground raw cannabis plant material 310 has been placed into mesh bags 312 which are immersed in the chilled water 314. The agitator 223 stirs the water with the bags, allowing the trichomes to break away from the rest of the plant matter.

Various numbers of filters and various sizes of filters can be used in the process in other embodiments. The sizes of the filters are from 1 to 250 µm. The filter mesh sizes are chosen in regards to the size of the trichomes that are typically desired. For example, in one embodiment, there may be just a single filter with a 75 µm mesh that is emptied regularly, or which has a relatively larger capacity, although it would be expected to be less effective than a series of filters.

The filters may be arranged in a vertical tower, or they may be separate.

The chilled water used for mixing with the ground raw cannabis plant material is, in some embodiments, from a different source than the water used for chilling the cooling jacket 216 of the mixing vessel 206.

The grinding may be carried out using a mesh size that is larger or smaller than the specific range given herein. However, care should be taken not to grind the trichomes, and not grind the raw plant matter so finely that significant amounts of it are ultimately collected with the trichomes. Also, the mesh size of the grinder should not be so large as to cause clogging of the apparatus. Nevertheless, in some embodiments, the initial grinding step is omitted.

In some embodiments, a 100 L mixing vessel is used, with 2-5 kg of biomass. In other embodiments, a 500 L or 1000 L conical mixing vessel is used. The selected sizes depend on the scale of the extraction process.

Temperatures that have been given to the nearest degree include all temperatures within a range of ±0.5° C. of the given value, where physically possible. Dimensions that have been given to the nearest 0.1 cm include all dimensions within a range of ±0.5 cm of the given value.

In general, unless otherwise indicated, singular elements may be in the plural and vice versa with no loss of generality.

Throughout the description, specific details have been set forth in order to provide a more thorough understanding of the invention. However, the invention may be practiced without these particulars. In other instances, well known elements have not been shown or described in detail and repetitions of steps and features have been omitted to avoid unnecessarily obscuring the invention. For example, various pumps, valves, jackets and lines are not shown for clarity. Accordingly, the specification and drawings are to be regarded in an illustrative, rather than a restrictive, sense.

It will be clear to one having skill in the art that further variations to the specific details disclosed herein can be made, resulting in other embodiments that are within the scope of the invention disclosed. Some steps in the flowchart may be performed in a different order, other steps may be added, or one or more steps may be removed without altering the main outcome of the process. All parameters, dimensions, materials, and configurations described herein are examples only and may be changed depending on the specific embodiment. Accordingly, the scope of the invention is to be construed in accordance with the substance defined by the following claims.

The invention claimed is:

1. A process for separating trichomes from raw *cannabis* plant material comprising:
   grinding the raw *cannabis* plant material using a mesh size between 1 cm and 2.5 cm to result in ground raw *cannabis* plant material;
   adding water at a temperature below 10° C. to the ground raw *cannabis* plant material to form a mixture;
   agitating the mixture to separate trichomes from the ground raw *cannabis* plant material;
   straining the mixture using a coarse mesh with a pore size of 200-1000 µm to separate the mixture into a trichome filtrate and unwanted *cannabis* plant matter;
   filtering the trichome filtrate to retain a residue of trichome-rich *cannabis* plant matter; and
   drying the trichome-rich *cannabis* plant matter to form a powder.

2. The process of claim 1, wherein the temperature of the water is 0-5° C., the process comprising maintaining the water at a temperature between 0-5° C.

3. The process of claim 1, wherein the mixture is agitated by feeding bubbles of gas through the mixture.

4. The process of claim 1, wherein the mixture is agitated for a duration between 5 and 120 min.

5. The process of claim 1, wherein the powder has a higher percentage content in trichomes than the raw *cannabis* plant material.

6. The process of claim 1, comprising drying the raw *cannabis* plant material to a moisture content of ≤10% before the grinding step.

7. The process of claim 1, wherein the mixing is done in a mixing vessel that has a jacket at a temperature of ≤10° C.

8. The process of claim 7, wherein the filtering comprises filtering the trichome filtrate, in order, through:
   a first filter with a pore size of 180-212 µm;
   a second filter with a pore size of 150-180 µm;
   a third filter with a pore size of 106-150 µm;
   a fourth filter with a pore size of 75-90 µm;
   a fifth filter with a pore size of 63-75 µm;
   a sixth filter with a pore size of 32-53 µm; and
   a seventh filter with a pore size of 15-32 µm.

9. The process of claim 7 comprising pressurizing the trichome filtrate while filtering.

10. The process of claim 7 comprising collecting separately from each filter a portion of the residue of trichome-rich *cannabis* plant matter.

11. The process of claim 7, wherein the filtering comprises filtering the trichome filtrate, in order, through a series of filters of increasing mesh number, starting with a first filter with a mesh number of 60 and ending with a final filter with a mesh number of 230.

12. The process of claim 1 comprising drying the trichome-rich *cannabis* plant matter in an oven set at a temperature between 30-40° C.

13. The process of claim 12, wherein the powder has a water percentage content by weight inferior to 10%.

14. The process of claim 1 comprising decarboxylating the powder in an oven set at a temperature of 115-120° C. for 30 min.

15. The process of claim 1, wherein the mixture is agitated with a blunt agitator that rotates at a speed of 50-500 rpm.

16. The process of claim 1, wherein the ground raw *cannabis* plant material is frozen.

17. The process of claim 1, comprising:
   placing the ground raw *cannabis* plant material into a bag made from the coarse mesh prior to adding the water;
   wherein the mixture is agitated while the raw ground *cannabis* plant material is in the bag.

18. The process of claim 17, wherein the bag is nylon.

* * * * *